(12) United States Patent
Butler et al.

(10) Patent No.: US 6,490,910 B1
(45) Date of Patent: Dec. 10, 2002

(54) APPARATUS AND A METHOD FOR INVESTIGATING THE PROPERTIES OF A SOLID MATERIAL BY INVERSE CHROMATOGRAPHY

(75) Inventors: David A. Butler, London (GB); Carl Levoguer, Twyford (GB); Daryl R. Williams, Burnham (GB)

(73) Assignee: Surface Measurement Systems Limited, London (GB)

( * ) Notice: Subject to any disclaimer, the term of this patent is extended or adjusted under 35 U.S.C. 154(b) by 0 days.

(21) Appl. No.: 09/830,089

(22) PCT Filed: Oct. 8, 1999

(86) PCT No.: PCT/GB99/03328

§ 371 (c)(1),
(2), (4) Date: Apr. 23, 2001

(87) PCT Pub. No.: WO00/25129

PCT Pub. Date: May 4, 2000

(30) Foreign Application Priority Data

Oct. 23, 1998 (GB) .................................................. 9823311

(51) Int. Cl.[7] ........................ G01N 25/02; G01N 31/08; G01N 30/02; B01D 15/08
(52) U.S. Cl. .................. 73/23.42; 73/23.35; 73/864.33; 422/70; 210/660
(58) Field of Search ........................... 73/23.42, 23.35, 73/19.02, 864.33, 864.72; 137/89; 210/656, 660; 422/70, 89

(56) References Cited

U.S. PATENT DOCUMENTS

| | | | | |
|---|---|---|---|---|
| 4,133,640 A | * | 1/1979 | Clinton et al. | 23/230 PC |
| 4,309,898 A | * | 1/1982 | Horton | 73/23.42 |
| 4,373,549 A | * | 2/1983 | Nalepa et al. | 137/487.5 |
| 4,534,207 A | * | 8/1985 | Szakasits et al. | 73/23.39 |
| 4,553,985 A | * | 11/1985 | Dahlgren et al. | 55/67 |
| 4,670,220 A | * | 6/1987 | Wells | 422/103 |
| 4,806,315 A | | 2/1989 | Daigle | 422/89 |
| 4,869,093 A | | 9/1989 | Gilbert | 73/23.1 |
| 4,991,423 A | * | 2/1991 | Poshemansky et al. | 73/23.35 |
| 5,268,302 A | * | 12/1993 | Rounbehler et al. | 436/96 |
| 5,610,835 A | * | 3/1997 | Dominguez et al. | 364/497 |
| 6,311,544 B1 | * | 11/2001 | Bertrand | 73/23.35 |

FOREIGN PATENT DOCUMENTS

| | | |
|---|---|---|
| EP | 0 745 845 | 12/1996 |
| EP | 0 745 845 A2 | 12/1996 |

OTHER PUBLICATIONS

Voelkel et al., "Examination of surfaces of solid polymers by inverse gas chromatography: 1. Dispersive properties," Polymer 37(3):455–462 (1996).

(List continued on next page.)

Primary Examiner—Hezron Williams
Assistant Examiner—David J. Wiggins
(74) Attorney, Agent, or Firm—Pillsbury Winthrop LLP

(57) ABSTRACT

Inverse gas-chromatography apparatus for investigating the properties of a solid material, having a carrier fluid, comprising at least two fluid components (typically water and an inert gas); a second flow comprising the carrier fluid components and probe material; a temperature controlled column, for holding the solid material; a switch for selectively passing the flow of carrier fluid and the second fluid flow through the column; a detector for detecting the passage of the probe material through the column. The relative proportions of the fluid components in the flow of carrier fluid and the second fluid flow can be controlled.

33 Claims, 4 Drawing Sheets

OTHER PUBLICATIONS

Zeki Y. Al–Saigh, "The Characterization of Polymer Blends by Inverse Gas Chromatography," TRIP (3):97–102 (1997).

Tihminlioglu et al., "Application of inverse gas chromatography to the measurement of diffusion and phase equilibria in polyacrylate–solvent systems," J. Chromatogr. A.845:93–101 (1999).

Pand S et al: "Mass Spectrometric Inverse Gas Chromatography Investigation of Polymeric Phase Transitions" Analytical Chemistry,US,American Chemical Society, Columbus, vol. 69, No. 13, Jul. 1, 1997, p. 2485–2495 XP000696560 ISSN: 0003–2700, abstract; Figure 1.

Al–Saigh Z Y: "The Characterization of Polymer Blends by Inverse Gas Chomatography" Trends in Polymer Science, NL, Elsevier Science Publishers B.V. Amsterdam, vol. 5, No. 3, Mar. 1997, p. 97–102 XP004055242 ISSN : 0966–4793, p. 97.

Voelkel A et al: "Examination of surfaces of solid polymers by inverse gas chromatography; 1. Dispersive properties" Polymer, GB, Elsevier Science Publishers B.V., vol. 37, No. 3, 1996, p. 455–462 XP004065448 ISSN: 0032–3861, p. 455.

Tihminlioglu F et al: "Application of inverse gas chromatography to the measurement of diffusion and phase equilibria in polyacrylate–solvent systems" Journal of Chromatography A, NL., Elsevier Science, vol. 845, No. 1–2, Jun. 11, 1999, p. 93–101 XP004170343, ISSN; 0021–9673, p. 93–94.

* cited by examiner

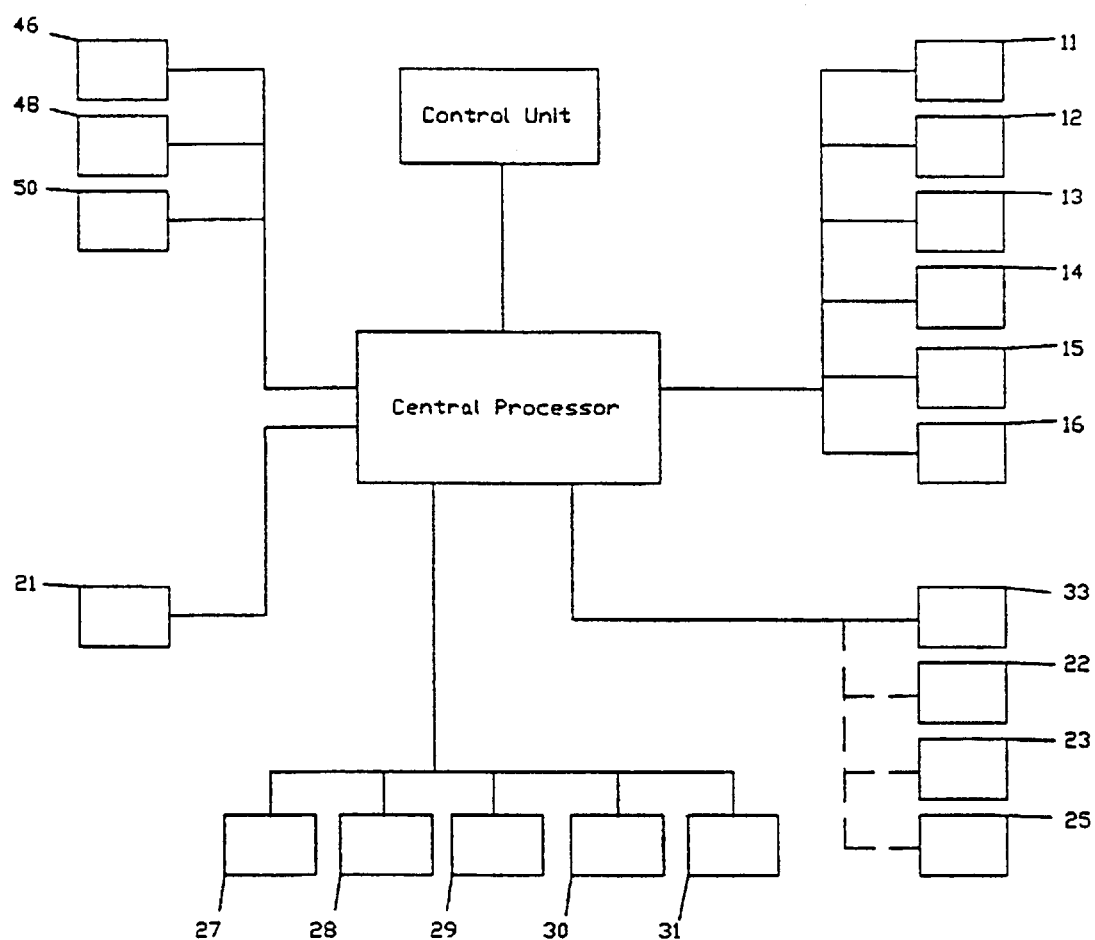

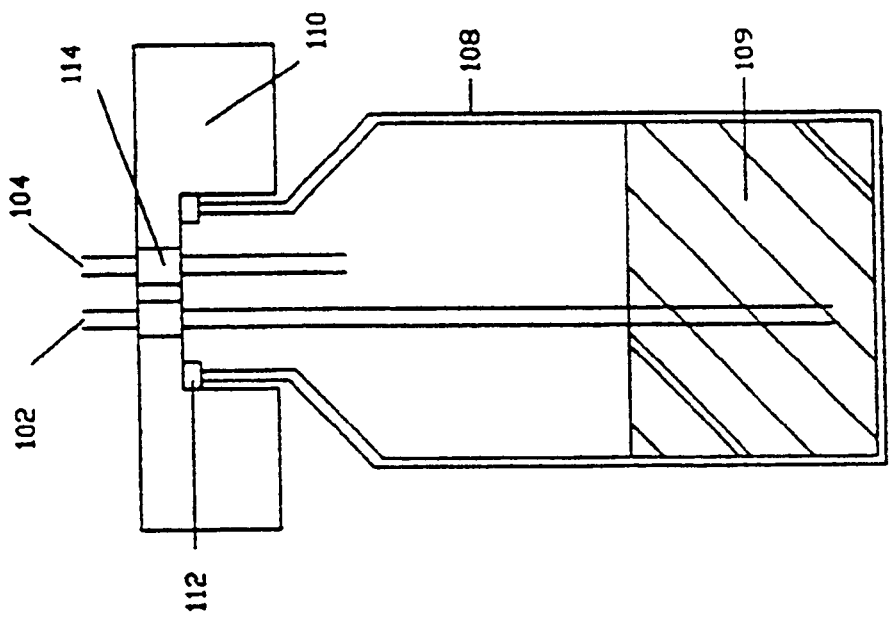
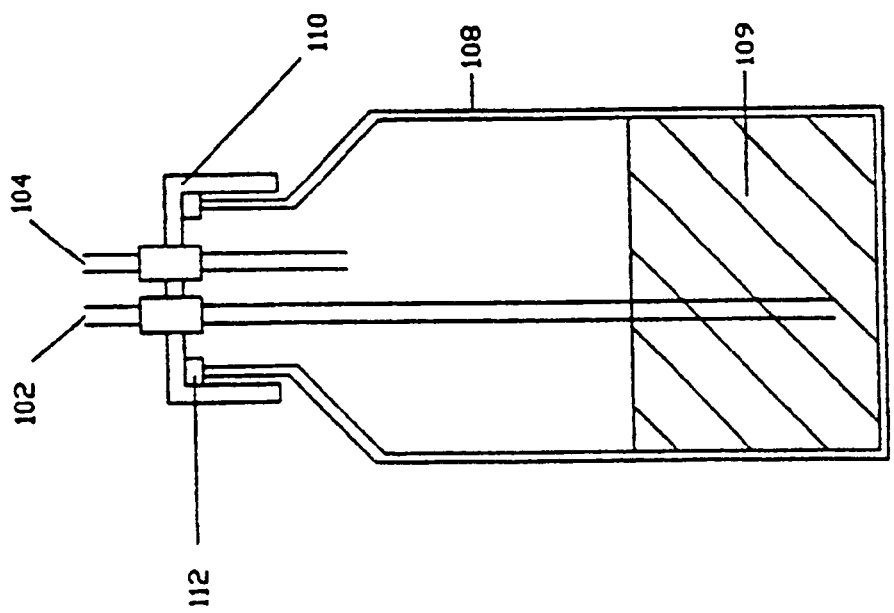

APPARATUS AND A METHOD FOR INVESTIGATING THE PROPERTIES OF A SOLID MATERIAL BY INVERSE CHROMATOGRAPHY

This application is the National Phase of International Application PCT/GB99/03328 filed Oct. 8, 1999 which designated the U.S. and that International Application was Published under PCT Article 21(2) in English.

The invention relates to apparatus and a method for investigating the properties of a solid material by inverse chromatography, and in particular by inverse gas chromatography.

In conventional gas or liquid chromatography, the composition of an unknown multicomponent gas or liquid is determined by injecting the unknown material into a carrier fluid (the "mobile phase", typically helium or nitrogen) which passes through an absorptive column (the "stationary phase"). The retention time due to mobile-stationary phase interactions (solid-vapour, vapour-liquid or solid-liquid adsorption) of the various eluted components allows for the composition of the unknown material to be deduced by reference to calibration data. In contrast, in inverse gas or liquid chromatography the properties of an unknown solid material in a column are investigated by passing a known probe through the column. For inverse gas chromatography, the carrier again is typically an inert gas such as helium or nitrogen, and the probe may be a material which is a gas under ambient conditions, or a solvent vapour.

The length of time that the probe is retained in the column is determined by the physicochemical interactions between the probe and the solid material packed in the column. This interaction is governed by a number of mechanisms, the most important of which are surface adsorption, and where the probe is partially soluble in the solid material, bulk solubilisation. Thus, the study of the retention behaviour of a probe can provide important information on the surface and bulk properties of the material in the column.

The use of inverse gas chromatography in investigating various properties of solids, such as adsorption isotherms, adsorption thermodynamics, surface energetics, acid-base interactions, glass transition temperatures, surface area, diffusion coefficients and porosity is described in the book "Physicochemical Measurement by Gas Chromatography" by J. R. Conder and C. L. Young., John Wiley & Son, 1979 and the article "Daryl Williams, Inverse Gas Chromatography, Characterisation of Composite Materials: Materials Characterisation Series—Surfaces, Interfaces, Thin Films, Chapter 5, 80–103 Butterworth-Heinemann, 1994. This article also discusses in detail the most appropriate experimental method, for example "elution at infinite dilution", "elution of a characteristic point" or "frontal analysis", for determining each of these properties. In addition to influencing the method chosen, the nature of the property under examination will also affect the choice of probe.

In most instruments used for inverse gas chromatography, the probe is a single compound which is introduced into a single component carrier gas flow that is then eluted through the column. For example, J. Chrom. A. 715, 1995, 279–285 discloses an injection system for an inverse gas chromatograph composed of a closed loop vapourisation chamber with a gas sampling valve, which provides multiple injections of the same sample into a single component gas flow at precisely controlled intervals.

A further variation is disclosed in U.S. Pat. No. 4,806,315 (Daigle). This reference is concerned with the ability to measure samples containing water more accurately by adding water vapour to the carrier gas flow, to form in effect, a two component carrier gas flow (e.g., water and helium). However, in the method disclosed, water passes into the flow via a water permeable membrane, and therefore the ratio of the two components (i.e., the humidity of the carrier) is fixed by the physical properties of the membrane. The only way to vary the humidity of the carrier is to dismantle the equipment and replace the membrane with one of a different type and size.

U.S. Pat. No. 4,869,094 (Gilber) relates to a method of determining sorption isotherms of food by inverse gas chromatography. In the method disclosed, a temporary front of water is established in a carrier gas which can be regarded as a two component gas flow composed of water and carrier gas. Although this reference discloses the possibility of investigating the behaviour of a solid material through inverse gas chromatography, under conditions of humidity, it does not disclose any method by which the humidity level can be varied. The two component carrier flow is formed by passing helium through a water trap, and thus the humidity of the flow is fixed at 100%. The only way therefore of changing the concentration of water vapour in the gas flow would be to change the temperature of the water bath surrounding the pre-column and the experimental column. This would, of course, necessitate a change in the temperature of the sample in the column, thereby influencing the behaviour of the material in the column since adsorption phenomena are highly temperature dependant.

According to the present invention there is provided apparatus for investigating the properties of a solid material comprising:

means for generating a flow of a carrier fluid, comprising at least two fluid components;

means for generating a second fluid flow comprising the said carrier fluid components and probe material;

a column, for holding the solid material;

means for selectively passing the flow of carrier fluid and the second fluid flow through the column;

means for controlling the temperature of the column;

a detector for detecting the passage of the probe material through the column, and means for controlling the relative proportions of the said fluid components in the flow of carrier fluid and the second fluid flow.

Preferably, the carrier fluid is a gas. The probe material may be a gas under normal conditions (e.g. methane) or may be a vapour of a substance normally liquid under normal conditions (e.g. octane).

In a particular preferred embodiment of the invention, one of the said carrier fluid components is water i.e. the means for controlling the relative proportions of the carrier fluid components comprises means for controlling the relative humidity of the carrier and second fluid flows. The ability to vary the humidity of the carrier enables the solid material to be investigated under a wide range of conditions and enables the simulation of conditions which may arise in use. This is particularly important where for example, the solid material is a compound intended for pharmaceutical use.

In another embodiment of the invention the means for generating a flow of carrier fluid comprises:

means for generating a first sub-flow relatively rich in a first said component (for example a stream of an inert gas such as helium);

means for generating a second sub-flow relatively rich in a second said component (for example a saturated stream of the same gas);

means for combining the first and second sub-flows,
wherein the means for controlling the relative proportions of the said fluid components comprises at least one control valve for varying the mixing ratio of the said first and second sub-flows (for example so as to control the humidity of the carrier).

In a further preferred embodiment, a third sub-flow, relatively rich in the probe material is also provided (for example, of humidified helium containing the desired probe material) and mixed with the first and second sub-flows in a desired ratio.

It is therefore possible for variations in the proportions of the carrier components to be made without the need to vary other experimental parameters such as column temperature. Furthermore, since the proportion of components present is not predetermined by the intrinsic properties of the apparatus, as in U.S. Pat. No. 4,806,315, but rather is varied simply by adjusting a control valve, the relative proportions of the fluid components may be varied both before and during an investigation.

Preferably, the second sub-flow comprises both the first and second components (for example, inert gas and water vapour) and the means for generating the second sub-flow comprises a container for the second component in liquid form. The container has an inlet connected to a fluid line, and a vapour space over the liquid, so that a flow of the said first component can be passed through the vapour space, and thereby generate the "sub-flow" through the said vapour space.

The said inlet will generally be below the liquid level of the second component, so that the first component (the inert gas) bubbles through the second component, on passage through the container.

In a further embodiment of the invention, a second fluid flow (i.e. a probe-containing flow) may be generated in a similar fashion, by bubbling gas through the probe material in liquid form. In this embodiment, the apparatus comprises at least one second container, for containing the probe material in liquid form, the said container having an inlet and an outlet, and means defining a vapour space over the said liquid probe material. A fluid line is connected to the second inlet, for passing a flow of at least one of the carrier flow components through the vapour space.

In this embodiment, the inlet is again preferably below the level of the probe material, so that the first component bubbles through the said probe material, on passage through the container.

By providing more than one such container for different probe material, with appropriate switching arrangements, it becomes possible to switch easily between various types of probe material.

Control valves, which may preferably be operated automatically, under computer control, may be provided for varying the mixing ratio of the said first, second and third sub-flows.

Because the relative proportions of the fluid components in the second fluid flow are varied by altering the mixing ratio of the various sub-flows, any changes to the concentration of components in the fluid flow can be brought about independently of, for example, the temperature of the column.

When the probe is a material which is a gas under normal conditions, the means for generating a second sub flow may comprise simply a fluid line for introducing the probe material, and the means for controlling the relative proportions of the said fluid components may comprise a control valve for varying the mixing ratio of the said probe material and the said two fluid components.

The apparatus may also include an injection port for injecting probe material into the carrier gas flow.

The apparatus in its preferred embodiments permits more than one method of introducing probe material into the carrier gas flow. This allows a number of different types of compounds to be employed as probes.

It is preferable that the apparatus comprises at least two columns since this enables the results from a column packed with the solid material under investigation to be compared with those from an empty column or one containing inert material, and for batch to batch variations and the reproducibility of samples and methods to be examined under identical conditions. A column selector valve may be employed to select the column into which the probe-containing flow is to be passed. A selector valve may also be employed to select the flow which is passed to the column or column selector valve, the selection being made, for example, between a probe-containing flow, and a non-probe-containing flow, the flow which it not selected at any particular time being vented from the apparatus.

In a preferred embodiment, probe-containing flow may be passed though one of the columns, whilst non-probe-containing flow, is passed through another. In this way, one column can be prepared for use while an experiment is being carried out on another column. This is of advantage to an operator since a packed column often needs to be conditioned for several hours or days to allow it to equilibrate before an experiment can be commenced.

The apparatus preferably includes at least three, more preferably, at least 4, and more preferably still, at least 5 temperature zones, and means for controlling independently the temperature in each said zone.

This enables those portions of the apparatus within a particular zone to be set at an optimum operating temperature, rather than a "compromise" temperature under which all parts of the apparatus can function.

In particular, the column and the flow selector valve are preferably in different temperature zones. The column is preferably also in a different temperature zone from the part of the apparatus in which the probe is introduced, particularly when a probe-containing flow sub-flow is generated from a liquid probe material.

The temperature of the zone or zones containing liquid probe material is determined by the physical properties of the fluid components employed, for example its boiling point. However, in order to investigate a wide range of solid material properties, it is desirable to be able to vary the column temperature over a considerably broader range. Thus, the ability to locate the liquid probe material in a different temperature zone from the column provides a considerable advantage.

The column and the injection port are preferably also in different temperature zones.

In a particularly preferred embodiment, the container for the second component (e.g. water) and the container for liquid probe material are in a first temperature zone, the column is in a second temperature zone, and the injection port and selector valves are in a third temperature zone.

It is also advantageous for the various selector valves to be located in different temperature zones from containers for the second component (e.g. water) and for liquid probe material, in order to minimise the risk of condensation of fluid components.

In a further particularly preferred embodiment, the container for the second component (e.g. water) and the container for liquid probe material are in a first temperature zone, the column is in a second temperature zone, the injection port is in a third temperature zone, and the flow selector valves are in a fourth temperature zone.

Where the carrier fluid is a gas, it is an advantage for the injection port to occupy a different temperature zones, since this enables its temperature to be maintained at which allows for the complete vaporisation of any liquid to be introduced through the injection port.

The temperature of the column can preferably be varied from ambient (~298 K) to 100° C. (373 K), preferably from 77 to 500 K, and more preferably from 77 to 600 K. The apparatus preferably also comprises means for pre-setting the temperature of at least one of the said temperature zones prior to an investigation of the properties of the said solid material.

The automatic control function of the apparatus may preferably comprise means for pre-programming flow of carrier fluid and the second fluid flow through the column prior to an investigation of the properties of the said solid material, and/or for pre-programming the relative proportions of the said fluid components prior to an investigation of the properties of the said solid material.

The ability to pre-set the experimental conditions allows the apparatus to be programmed to carry out a number of experiments in a row, for example overnight, thus maximising the efficient use of time.

The proportion of each fluid component in the flow of carrier fluid and the second fluid flow can preferably be varied over a range of from 0 to 95 percent, by altering the mixing ratio of the various sub-flows. The concentration of components present may be thus be varied in a step-wise, ramped or modulated manner.

The principal component of the carrier will generally be an inert gas, such as nitrogen, helium or argon, and the probe material will generally comprises at least one organic compound.

In a further preferred embodiment of the invention, the column is straight and is vertically mounted in such a way that the longitudinal axis of the column is vertical.

The use of a straight column allows the column to be packed more easily without gaps or breaks forming during packing. Furthermore, mounting the column vertically prevents gaps or channels developing if the solid material settles during conditioning since any settling will simply shorten the packed length of solid material.

It can therefore be seen that the apparatus is particularly suited for a determining a wide range of properties of a solid material in the column since it is capable of generating a wide range of operating conditions.

Appropriate software may be provided to automate the measurement of, for example, net retention time, net retention volume, specific retention volume, column inlet and outlet pressures, and fluid-solid distribution coefficient, and for determining therefrom properties of the solid material such as heat of adsorption, standard free energy of adsorption, entropy of adsorption, dispersive component of solid surface energy, total uptake per unit of solid material, surface area, thermal desorption, glass transition temperature, phase transition properties, diffusion coefficients, porosity, polymer-polymer interaction parameters, probe-polymer interaction parameters, acid-base surface properties and competitive adsorption.

In another aspect of the invention there is provided, a method of investigating the properties of a solid material comprising:

inserting the solid material into the column of apparatus as described above;
passing the flow of carrier fluid over the solid material;
passing the second fluid flow over the solid material;
detecting the passage of probe material through the column to determine properties of solid material.

A number of preferred embodiments of the present invention will now be illustrated with reference to the accompanying drawing in which:

FIG. 2 is a block schematic diagram of an inverse gas chromatograph according to the invention.

FIG. 3 is a side sectional view of a saturator according to the invention.

FIG. 3a is a similar side sectional view, showing a preferred lid arrangement.

Figure 1:
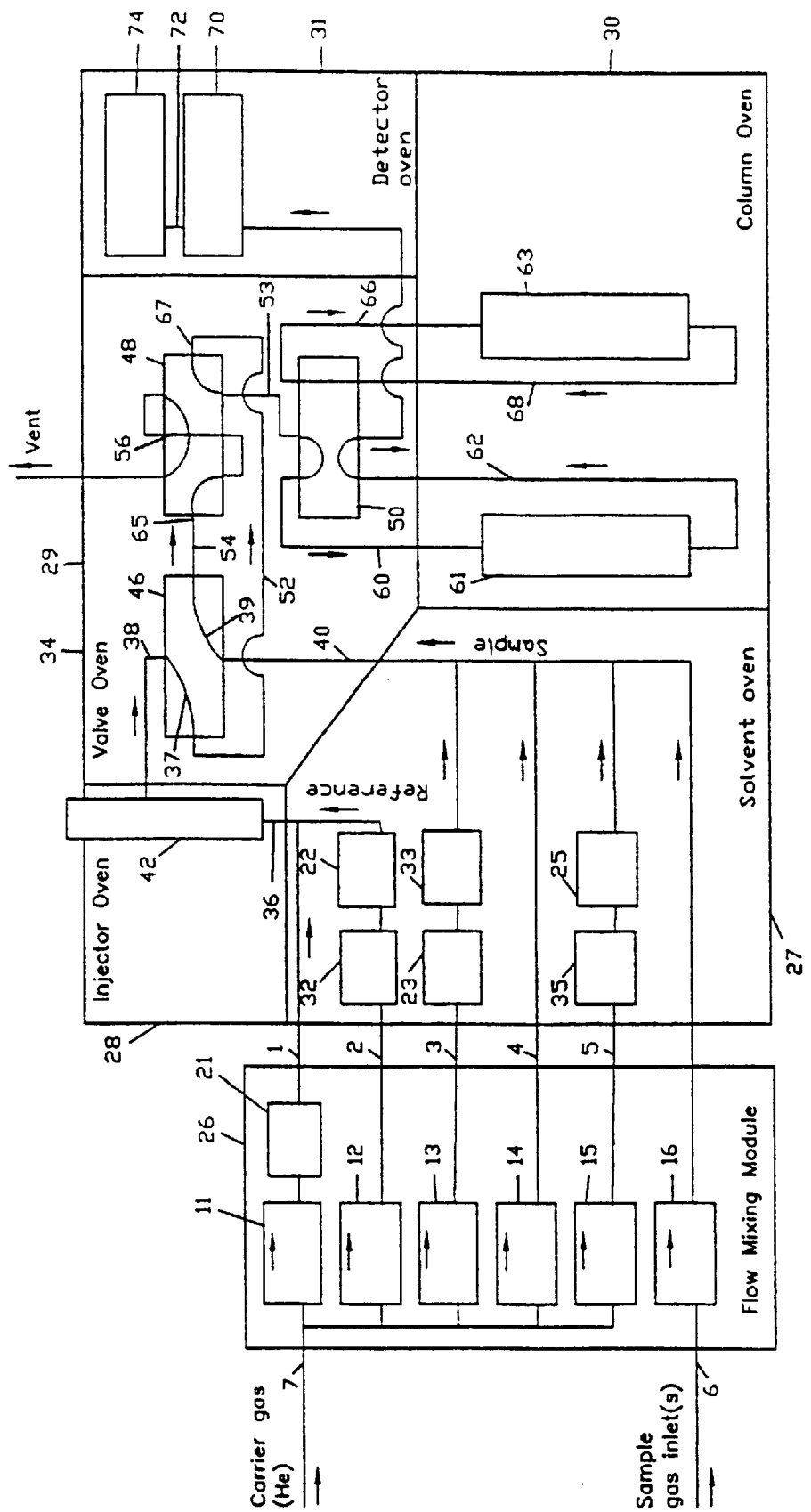
FIG. 1 is a schematic diagram of a preferred embodiment of an inverse gas chromatograph for investigating the properties of a solid material according to the invention.

FIG. 1 shows an inverse gas chromatograph according to the invention having a flow mixing module 26, and an oven module 34. oven module 34 comprises a solvent oven 27, an injector oven 28, a valve oven 29, a column oven 30 and a detector oven 31. A fluid line 7, provides a supply of carrier gas (usually helium) and is connected to flow control valves 11, 12, 13, 14 and 15. Fluid lines 1 to 5, are connected to the outlets of flow control valves 11 to 15 respectively, and pass out of the flow mixing module 26 and enter the solvent oven 27.

A further fluid line 6, provides a supply of gaseous probe material, for example methane, and is connected to a flow control valve 16 in the flow mixing module 26.

The fluid line flow control valves 11 to 16 can be used to control the sub-flows through each of lines 1 to 6, which can be combined in various combinations, depending upon the settings of flow control valves 11 to 16, and valves 46, 48 and 50, which will be described in more detail hereinafter.

The sub-flow in line 4 consists of pure helium gas and is passed directly to the inlet of stream selection valve 46.

FIG. 3 shows the saturators 32 and 35 which each comprise an inlet 102, an outlet 104 and a container 106, consisting of a bottle 108 and a lid 110. In a preferred embodiment lid 110 takes the form of a stainless steel plate, as shown in FIG. 3a. A liquid such as water may be placed into the bottle 108 prior to use via the lid 110, and an air tight seal is formed between the lid 110 and the bottle 108 by seals 112.In the preferred embodiment of FIG. 3a, the bottle 108 screws into stainless steel plate 110, and the various fittings are welded, to minimise the likelihood of leaks. The inlet 102 and the outlet 104 pass into the sealed bottle 108 via two connectors 114 in the lid 110. The sub-flows 2 and 5 are connected to the inlets of respective saturators 32 and 35 and the inlets and outlets are positioned so that when the saturators are in use gas bubbles through the water in the container.

Figure 4:
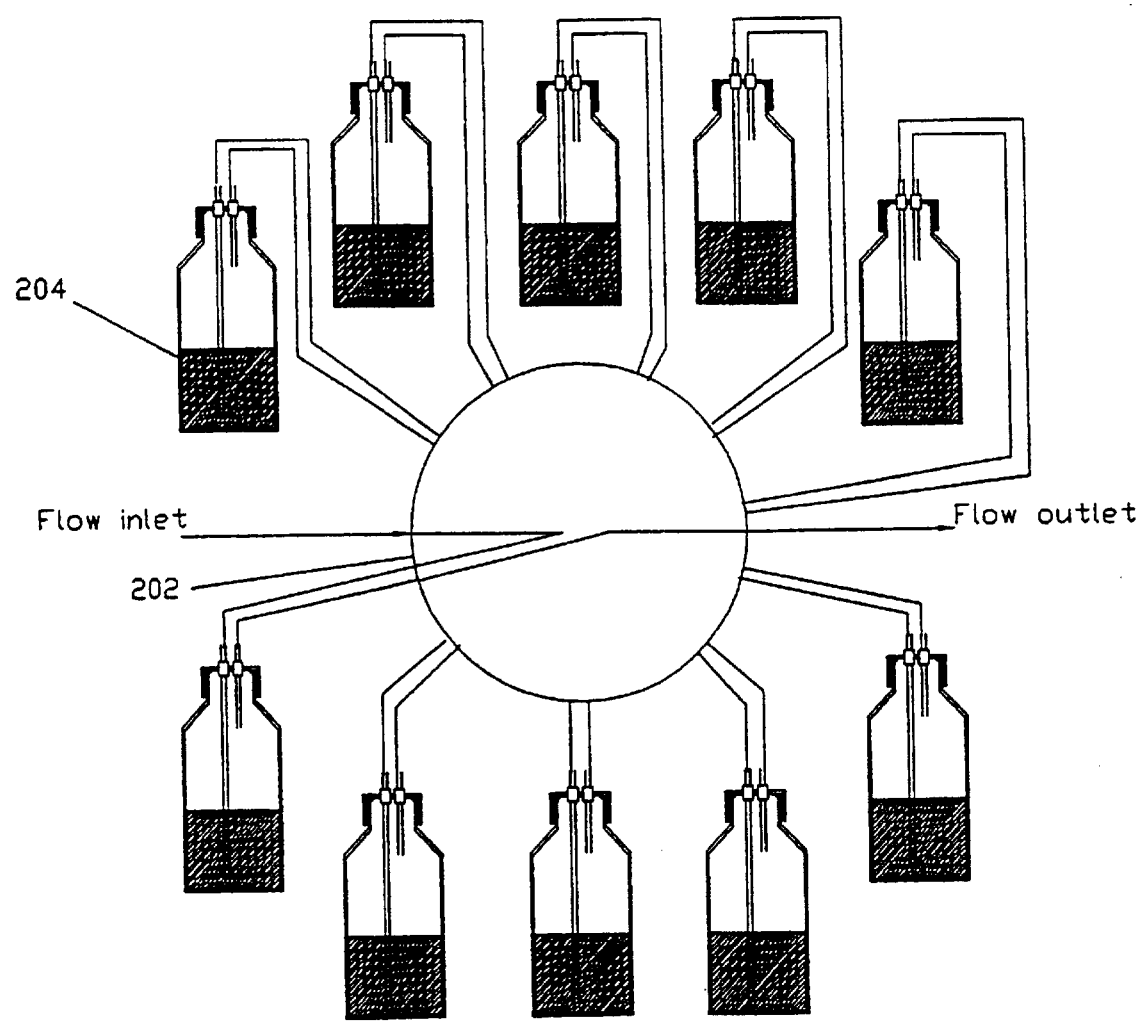
FIG. 4 is a schematic diagram of a saturator carousel according to the invention.

Fluid line 3 is passed to a saturator carousel 33. Saturator carousel 33 (FIG. 4) consists of a 10-position valve (202), each valve position being provided with a saturator (204) of the same general type as saturators 32 and 35. The saturators contain various volatile liquids, e.g. octane, heptane etc., the vapours of which constitute alternative probe materials. Each saturator unit can be selectively connected to the fluid line 3 by switching the position of the ten position valve. optionally, one position can be set as a blank.

Check valves 21, 22, 23 and 25 are provided in lines 1, 2, 3 and 5 respectively in order to prevent back flow and mixing of fluid components. Alternatively, valve 21 may be an electrically operated solenoid valve, and valves 22, 23 and 25 may be omitted.

Also within the solvent oven 27, fluid lines 1 and 2 rejoin to form a single fluid line 36, connected to the inlet of a manual injection port 42, in injection oven 28. Similarly, fluid lines 3 to 6 reconnect to form fluid line 40. A fluid line 38 from the manual injection port 42 is connected to a stream selection valve 46 in the valve oven 29. Fluid line 40 is similarly connected to a second inlet of valve 46. Optionally, the solvent oven 27 contains a fail safe device (not shown) which can detect any leak of solvent vapour and disconnect the power supply to the oven modules in the event that a leak is detected.

Stream selection valve 46, located in valve oven 29 enables the flows in lines 38 and 40 to be switched alternatively between lines 52 and 54, connected to respective inlet ports 67 and 65 of the "injector" valve 48. A fluid line 53 is connected to an outlet port of injector valve 48 and to column selection valve 50. A 250 $\mu$l standard injection loop 56 connected to injector valve 48 may be switched into and out of the flow. When, as is shown in FIG. 1, the stream selection valve 46 is in a first position, the fluid line 36 is connected via a valve channel 37 to the fluid line 52 and the fluid line 40 is connected via a valve channel 39 to the fluid line 54. When the valve 46 is switched to a second position, fluid line 36 is connected via valve channel 37 to fluid line 54 and fluid line 40 is linked via valve channel 39 to fluid line 52.

In FIG. 1, when the injector valve 46 is shown in a first position, the flow in line 54 is passed through injection loop 56 to vent. When a second valve position is selected, the injection loop is switched into fluid line 53.

Adjacent to the valve oven 29 is a column oven 30 containing two columns 61 and 63, mounted in a metal block (not shown). The metal block is provided with heating and cooling elements. In a preferred embodiment these take the form of thermoelectric "Peltier" heaters, which enable accurate temperature control of any sample over the range of 0° C. to 150° C. Alternatively, cartridge heaters may be employed for heating, and a coolant flow (such as liquid nitrogen or $CO_2$) provided for cooling purposes. Such an arrangement can permit temperature control over the range of 77 K to 500 K. The column oven 30 also has a hinged door which allows easy access to metal block and to the columns 61 and 63, for removal and installation purposes.

Columns 61 and 63 are straight and are mounted vertically which facilitates their packing with a solid material and helps to prevent channels and gaps forming in the packing. Typically, stainless steel or glass columns, of approximately 220 mm or 250 mm in length and approximately 3 mm internal diameter, which have been passivated prior to installation with dimethyldichlorosilane (DCMS), are employed.

Fluid lines 60 and 66 are connected to the tops of columns 61 and 63, respectively, and to the column selector valve 50. Fluid lines 62 and 68 are connected to the bases of columns 61 and 63 respectively and the column selector valve 50.

After passage through the selected column gas passes through fluid line 64 extending from the column selector valve 50 to a thermal conductivity detector 70 in the detector oven 31. The thermal conductivity detector 70, which is sensitive to all organic vapours, water and air, is linked via fluid line 72 to a flame ionisation detector 74 which provides high sensitivity to organic vapours. optionally, the detector oven may also include a mass selection detector, for the identification of specific molecules in multi-component systems.

When the column selection valve 50 is in first position (as shown in FIG. 1) fluid line 53 is connected via a valve channel to fluid line 60 and fluid line 62 is linked via another valve channel to fluid line 64 whilst another valve channel forms a closed loop between with fluid lines 66 and 68. When the column selection valve 50 is switched to a second position, fluid line 53 is connected to fluid line 66 and fluid line 68 is connected to fluid line 64, and a closed loop is formed by fluid lines 60 and 62.

Typically, all fluid lines and compression fittings used throughout the apparatus are made of stainless steel, and valve seals consist of chemically resistant polymers.

The flow mixing module 26 and the oven modules 27 to 31 are linked to a computer programmed so as to independently control the temperature of each of the ovens 27 to 31, valve switching, the flow control valves 11 to 16 and the detector conditions before and during an experiment. The software also records and analyses experimental data such as the retention time of probe material in the column, column inlet pressure, column outlet pressure, flow rates of the flow of carrier fluid and the second fluid flow, column temperature and probe concentration in the mobile phase. In a particular embodiment of the invention, the software also calculates any one of net retention time of the probe material in the column, net retention volume, specific retention volume, mean column pressure, fluid-solid distribution coefficient and/or any one of the following properties of the solid material; heat of adsorption, standard free energy of adsorption, entropy of adsorption, dispersive component of solid surface energy, total uptake per unit of solid material, surface area, thermal desorption, glass transition temperature, phase transition properties, diffusion coefficients, porosity, polymer-polymer interaction parameters, probe-polymer interaction parameters and acid-base surface properties.

As mentioned previously, the type of investigation to be carried out will determine the reaction parameters such as the flow rates, the composition of any gas flow passed through the column, the relative proportions of any components in the gas flows, the extent to which the composition and relative proportions are to be varied during the course of an experiment, and the temperature at which the various ovens 27 to 30 need to be maintained. For example, information about adsorption thermodynamics or acid-base properties of the solid material being investigated is best obtained using a carrier/probe mixture into which low concentrations of probe has been injected. However, where, for example, adsorption isotherm data is required, the preferred experimental method involves perturbation of a constant probe concentration which have previously been established across the column, or step-wise changes in probe concentration.

A detailed description of the experimental conditions required to examine the surface and bulk properties of a solid material, and the theory involved in calculating the extent of these interactions from experimental data is given in aforementioned article by Daryl Williams, and the aforementioned book by J. R. Conder and C. L. Young.

Prior to any experiment being carried out using an inverse gas chromatograph according to the present invention, the solid material to be investigated must be packed into column 61 or column 63. The solid material may be prepared for packing by grinding and sieving it through a suitable mesh size. Finer mesh sizes (60–80, 80–100, 100–129 mesh) generally give longer retention times and a corresponding improvement in peak resolution. However, larger grains (30–40 mesh) may be more suitable for methods such as frontal analysis where a small column pressure drop is required.

Optionally, a packing device is provided which enhances the reproducibility of column packing. The device consists of a support for the column, which can be caused to oscillate vertically, typically with an adjustable period of form 0.1 to 10 Hz. In order to pack column 61 or 63 using this device, the empty column 61 or 63 is placed vertically in the device and a hopper on top of the column 61 or 63 is filled with prepared solid material. An electric solenoid controlled by an oscillator circuit with an adjustable period (0.1–10 Hz) and amplitude taps the column 61 or 63 from below in a vertical motion. By keeping the column 61 or 63 and the solenoid motion to a vertical orientation, any interaction of the material with the walls of the column 61 or 63, which causes packing problems, is reduced. The tapping is continued until the column 61 or 63 is filled and settling is complete. The column 61 or 63 can then be installed into the column oven 30. By using the same amplitude and period each time a column 61 or 63 is packed, the reproducibility of the packing is improved.

The apparatus may be used to carry out a number of experimental methods. In the description which follows, the experiments described employ helium as the "first component", and water vapour as the "second component" of the carrier gas, the water vapour being introduced using saturators 32 and 35. It will be appreciated however that in alternative embodiments, other substances may be employed either as the first or the second component, and that such saturators are not necessary if, for example the second component is a gas under ambient conditions.

According to a first method of operation, a reference flow of helium carrier gas having a selected humidity is established in fluid line 36, by appropriate adjustment of the relative sub-flows in lines 1 and 2, using flow control valves 11 and 12. If a reference flow consisting of pure helium is required, the flow control valve 12 is adjusted to prevent any flow through fluid line 2 into fluid line 36.

Flow control valves 14 and 15 are adjusted so as to provide sub-flows in lines 4 and 5 such that the flow in line 40 has the same humidity as that in line 36. A desired material is selected for use as a probe, using the saturator carousel, and a desired concentration of the probe material in the flow in line 40 is selected, by appropriate adjustment flow control valve 13.

The column oven 30, detector oven 31, solvent oven 27, the valve oven 29 and the injector oven 28 are each set so as to prevent water condensation in the various fluid lines.

By adjusting the flow control valves 11 and 12 and the temperature of the solvent oven 27, it is possible to vary the relative amount of each component of the reference flow such that the total amount of components other than carrier gas varies from 0 to 95%. It is therefore possible to generate a reference flow with a relative humidity of from 0 to 95%.

Similarly, the composition of the probe-containing flow can be controlled using flow control valves 13 to 16 on fluid lines 3 to 6. Again, the relative proportions of any of the components in the sample flow may be varied by from 0 to 95% by adjusting the flow control valves 13 to 16 and the temperature in the solvent oven. Thus, when the second component is water, it is also possible to vary the relative humidity of the sample flow at the column from 0 to 95%.

The flow control valves 11 to 16 can provide a controllable flow from 10 $cm^3 min^{-1}$ upwards, and are accurate to 1% of full scale. Optionally, more flow control valves, fluid lines and solvent saturators can be added to the apparatus to allow more complex flow mixtures to be prepared if desired.

It is also possible for probe material to be introduced into the reference flow by manual injection with a standard gas chromatography syringe when the reference flow in fluid line 36 passes through the manual injection port 42. During an experiment, the temperature of the injector oven 28 is maintained at a sufficient temperature to ensure vapourisation of any liquid injected through the port (usually approximately 80° C.)

Before a gas flow containing probe material is passed through column 61 or column 63, and the passage of the probe material detected, it may be necessary for the column to be preconditioned by passing a flow of gas comprising carrier gas and optionally a second component through the column for several hours or days.

When the stream selection valve 46 is in a first position (as shown in FIG. 1), the reference flow in fluid line 36 passes through the stream selection valve 46 via valve channel 37 and into fluid line 52. When the injector valve 48 is in the first position, again shown in FIG. 1, no sample flow is injected into the reference flow as it passes through the injector valve 48 into the column selection valve 50.

FIG. 1 shows the column selection valve 50 in a first position in which the reference flow is passed via fluid line 60 to column 61.

As can be seen from FIG. 1, when the stream selection valve 46 is in the first position, the sample flow in fluid line 40 passes via fluid line 54 to the standard 250 $\mu l$ injection loop 56. A sample is injected by switching the loop into the flow. On passing through column 61, the resulting gas flow passes to the thermal conductivity detector 70 and the flame ionisation detector 74 via fluid line 62, the column selection valve 50, and fluid lines 64 and 72, before passing to vent.

Alternatively, a continuous stream of the sample flow may be passed through either column 61 or 63 by switching stream selection valve 46 to the second position. Furthermore, by operation of the flow control valves 11 to 16, it is possible to generate flows in which the proportions of components can be varied in a stepwise, rammed or modulated matter. The maximum modulation speed is limited by the response time of the flow control valves 11 to 16 and is approximately 1 Hz.

As mentioned previously, the temperature of the valve oven 29 is maintained at approximately 40° C. above the temperature of the solvent oven 27 to prevent condensation in the valve capillaries.

Although FIG. 1 shows a particular valve arrangement of valves in the valve oven 29, it will be appreciated that other arrangements are possible which would allow for separate gas flows to be passed simultaneously through separate columns, thus enabling a particular column to be preconditioned whilst another is in experimental use. Similarly, a valve arrangement may be employed in which the same gas flow can be passed through several columns sequentially, to allow for batch to batch comparisons.

The apparatus according to the invention is useful for investigating various properties of solid materials by inverse chromatography. It is capable of generating flows of carrier fluid containing a wider range of components than could previously be produced with known inverse chromatography apparatus. For example, the apparatus allows for the generation of a carrier gas flow comprising two or more components, neither of which need be water, and the second fluid flow can contain the components of the carrier gas flow plus probe material consisting of at least two probe components. Furthermore, the apparatus enables the concentration of the components in the carrier and second fluid flows to be controlled before and during the course of an investigation.

Since the apparatus allows the investigation of the solid to be carried out under a range of conditions not previously available, a wider range of information about the properties of the solid material can be determined.

What is claimed is:

1. Apparatus for investigating the properties of a solid material comprising:
   means for generating a flow of a carrier fluid, comprising at least two fluid components;
   means for generating a second fluid flow comprising the said carrier fluid components and probe material;
   a column, for holding the solid material;
   means for selectively passing the flow of carrier fluid and the second fluid flow through the column;
   means for controlling the temperature of the column;
   a detector for detecting the passage of the probe material through the column, and
   means for controlling the relative proportions of the said fluid components in the flow of carrier fluid and the second fluid flow.

2. Apparatus according to claim 1, wherein the carrier fluid is a gas.

3. Apparatus according to claim 1, wherein one of the said carrier fluid components is water.

4. Apparatus according to claim 1, wherein the means for generating a flow of carrier fluid comprises:
   means for generating a first sub-flow relatively rich in a first said component;
   means for generating a second sub-flow relatively rich in a second said component;
   means for combining the first and second sub-flows; and
   wherein the means for controlling the relative proportions of the said fluid components comprises at least one control for varying the mixing ratio of the said first and second sub-flows.

5. Apparatus according to claim 4, wherein the second sub-flow comprises both the first and second components, and
   wherein the means for generating the second sub-flow comprises a container for the second component in liquid form, the container having a first inlet and a first outlet, and means defining a vapour space over the said liquid, and
   wherein the apparatus includes a fluid line connected to the first inlet, for passing a flow of the said first component through the said vapour space.

6. Apparatus according to claim 5, wherein the said first inlet is below the level of the said second component, such that the first component bubbles through the second component, on passage through the container.

7. Apparatus according to claim 1, wherein the means for generating a second fluid flow comprises at least one second container, for containing the probe material in liquid form, the said at least one container having a second inlet and a second outlet, and means defining a vapour space over the said probe material in liquid form, and wherein the apparatus includes a fluid line connected to the second inlet, for passing a flow of at least one of the said carrier flow components through the said vapour space.

8. Apparatus according to claim 7, wherein the said second inlet is below the level of the said probe material, such that the first component bubbles through the said probe material, on passage through the container.

9. Apparatus according to claims 7 and 8, wherein the means for generating a second fluid flow comprises a plurality of the said second containers and means for switching the carrier fluid flow between the said second containers.

10. Apparatus according to any one of claims 4 to 6, wherein the means for generating a second fluid flow comprises:
    means for generating the said first sub-flow, relatively rich in the first carrier component;
    means for generating the said second sub-flow, relatively rich in the second carrier component;
    means for generating a third sub-flow, relatively rich in the probe material;
    means for combining the first, second and third sub-flows; and
    wherein the means for controlling the relative proportions of the said fluid components comprises at least one control valve for varying the mixing ratio of the said first, second and third sub-flows.

11. Apparatus according to claim 10, wherein the said third sub-flow is a mixture of the said first component and the probe material.

12. Apparatus according to claim 1, wherein the means for generating a second sub-flow comprises a fluid line for introducing the probe material, and wherein the means for controlling the relative proportions of the said fluid components comprises a control valve for varying the mixing ratio of the said probe material and the said two fluid components.

13. Apparatus according to any one of claims 4 to 11 including a plurality of fluid lines, for the respective sub-flows, wherein the means for controlling the relative proportions of the said fluid components comprises a control valve on each fluid line for varying the mixing ratio of the respective sub-flows.

14. Apparatus according to claim 1, wherein the means for generating a second fluid flow comprises an injection port for injecting probe material into the carrier gas flow.

15. Apparatus according to claim 1, wherein the means for selectively passing the carrier fluid flow and the second fluid flow through the column comprises a valve for selecting the flow to be passed through the column, and an injection loop for injecting the selected flow into the column.

16. Apparatus according to claim 1, comprising at least two columns.

17. Apparatus according to claim 16, wherein the means for selectively passing the carrier fluid flow and the second fluid flow through the column comprises a valve for selecting the flow to be passed through the column, a valve for selecting the column into which the selected flow is to be passed, and an injection loop for injecting the selected flow into the column.

18. Apparatus according to claim 17, wherein the means for selectively passing the carrier fluid flow and the second fluid flow through the column comprises means for simultaneously passing the flow of carrier fluid and the second fluid flows through the said two columns.

19. Apparatus according to claim 1, including at least three temperature zones, and means for controlling independently the temperature in each said zone.

20. Apparatus according to claim 19 wherein the column and the means for selectively passing the flow of carrier fluid and the second fluid flow through the column are in different temperature zones.

21. Apparatus according to claim 19, wherein the column and the said container for the second component are in different said temperature zones.

22. Apparatus according to claim 7, including at least three temperature zones, and means for controlling independently the temperature in each said zone, wherein the second container and the column are in different said temperature zones.

23. Apparatus according to claim 22, wherein the said container for the second component and the said second container are in the same temperature zone.

24. Apparatus according to claim 19, and including an injection port for injecting probe material into the carrier gas flow wherein the column and the said injection port are in different said temperature zones.

25. Apparatus according to claim 5, including at least three temperature zones, and means for controlling independently the temperature in each said zone, and an injection port for injecting probe material into the carrier gas flow, wherein the said container for the second component and the said second container are in a first said temperature zone, the column is in a second said temperature zone, and the injection port and the means for selectively passing the flow of carrier fluid and the second fluid flow through the column are in a third said temperature zone.

26. Apparatus according to claim 5, including at least three temperature zones, and means for controlling independently the temperature in each said zone, and an injection port for injecting probe material into the carrier gas flow, wherein the said container for the second component and the said second container are in a first said temperature zone, the column is in a second said temperature zone, the injection port is in a third said temperature zone, and the means for selectively passing the flow of carrier fluid and the second fluid flow through the column is in a fourth said temperature zone.

27. Apparatus according to claim 1, comprising means for pre-programming the means for selectively passing the flow of carrier fluid and the second fluid flow through the column prior to an investigation of the properties of the said solid material.

28. Apparatus according to claim 1, comprising means for pre-programming the means for controlling the relative proportions of the said fluid components prior to an investigation of the properties of the said solid material.

29. Apparatus according to claim 1, wherein the means for controlling the relative proportions of the said fluid components in the flow of carrier fluid and the second fluid flow comprises means for varying the proportion of each fluid component in the flow of carrier fluid and the second fluid flow such that the total amount of components other than carrier gas varies from 0 to 95 percent.

30. Apparatus according to claim 1, wherein the probe material comprises at least one organic compound.

31. Apparatus according to any one of the preceding claims, wherein the column is straight and wherein the column is vertically mounted in such a way that the longitudinal axis of the column is vertical.

32. Apparatus according to claim 1, comprising:

means for recording the retention time of probe material in the column, column inlet pressure, column outlet pressure flow rates of the flow of carrier fluid and the second fluid flow, column temperature, probe concentration in the mobile phase; and means for calculating any one of net retention time of the probe-material in the column, net retention volume, specific retention volume, column pressure drop, fluid-solid distribution coefficient and/or any one of the following properties of the solid material; heat of adsorption, standard free energy of adsorption, entropy of adsorption, dispersive component of solid surface energy, total uptake per unit of solid material, surface area, thermal desorption, glass transition temperature, phase transition properties, diffusion coefficients, porosity, polymer-polymer interaction parameters, probe-polymer interaction parameters, acid-base surface properties and competitive adsorption.

33. A method of investigating the properties of a solid material comprising:

inserting the solid material into the column of the apparatus according to claim 1;

passing the flow of carrier fluid over the solid material;

passing the second fluid flow over the solid material;

detecting the passage of probe material through the column to determine properties of solid material.

* * * * *